Figure 1:
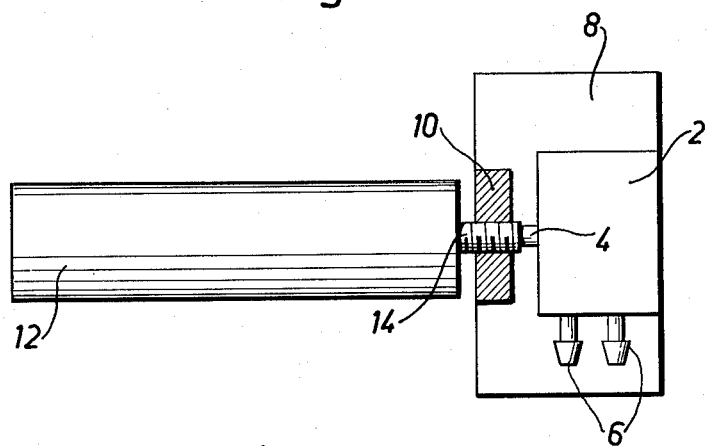

United States Patent [19]

Ekman

[11] 4,242,088
[45] Dec. 30, 1980

[54] REGULATING DEVICE FOR PRESSURE FLUID ACTUATED APPARATUS

[75] Inventor: Björn Ekman, Upplands Väsby, Sweden

[73] Assignee: Dental AB, Upplands Väsby, Sweden

[21] Appl. No.: 843,557

[22] Filed: Oct. 19, 1977

[30] Foreign Application Priority Data

Dec. 13, 1976 [SE] Sweden .............................. 7613985

[51] Int. Cl.³ ........................................... F16K 31/62
[52] U.S. Cl. .................................. 433/101; 251/295; 74/512; 137/362; 222/179
[58] Field of Search ................. 32/22; 251/278, 295; 74/512, 513; 222/179; 137/343, 362; 433/101

[56] References Cited

U.S. PATENT DOCUMENTS

| 1,468,378 | 9/1923 | Cummings | 74/513 |
| 1,494,910 | 5/1924 | Hench | 251/278 |
| 1,530,894 | 3/1925 | Hayes | 74/513 |
| 1,739,408 | 12/1929 | Medrano et al. | 251/295 |
| 2,069,349 | 2/1937 | Bergschicker | 74/513 |
| 2,235,850 | 3/1941 | Rubissow | 74/513 |
| 2,933,284 | 4/1960 | Yocum | 251/278 |
| 3,232,568 | 2/1966 | Lennon et al. | 137/343 |
| 3,305,207 | 2/1967 | Calderoni | 251/278 |
| 3,742,167 | 6/1973 | Müther | 74/512 |

FOREIGN PATENT DOCUMENTS 691711 8/1964 Canada ..................................... 74/513

*Primary Examiner*—Martin P. Schwadron
*Assistant Examiner*—H. Jay Spiegel

[57] ABSTRACT

Improved actuator for a control valve especially useful for a compressed air-operated dentist's drill comprises a foot actuated roller connected to provide axial movement through a screw threaded connection to a spring-biased valve control element.

5 Claims, 5 Drawing Figures

REGULATING DEVICE FOR PRESSURE FLUID ACTUATED APPARATUS

The present invention relates to a regulating device for pressure fluid actuated apparatus, which includes a valve for the pressurized fluid supply and a foot controlled operating device for a movable valve element of the valve.

In connection with pressurized air actuated dental drilling machines it has hitherto been difficult to provide for a continuous control or regulation of the drill speed. One of the reasons is the difficulty in finding a valve which, by means of foot or manual operation of the conventional type, allows for regulation that is sensitive enough. A very common type of air valve is e.g. the one in which the movable valve element is a spring loaded piston, and it is probably a general experience that it is difficult to manually provide for an accurate movement of a linearly movable object of that kind.

The object of the invention is to provide a regulating device of the kind defined initially that allows for an exact and accurate operation of the valve. A specific object of the invention is to provide such a regulating device which when used for pressurized air operated dental drilling machines in a simple way permits a continuous regulation of the drill speed.

The regulating device according to the invention is characterized in that the operating device consists of a rollable roller body, transmission means being arranged for transferring the rolling movement to a movement suitable to affect the valve element.

Figure 3:
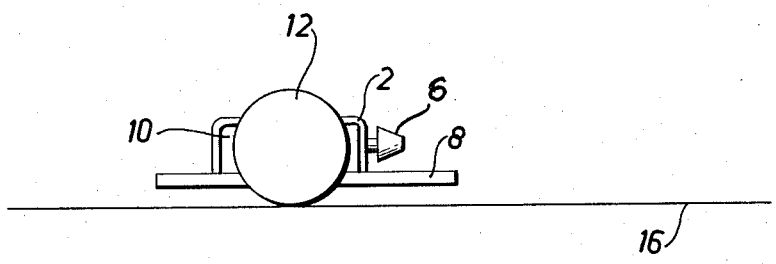
Figure 4:
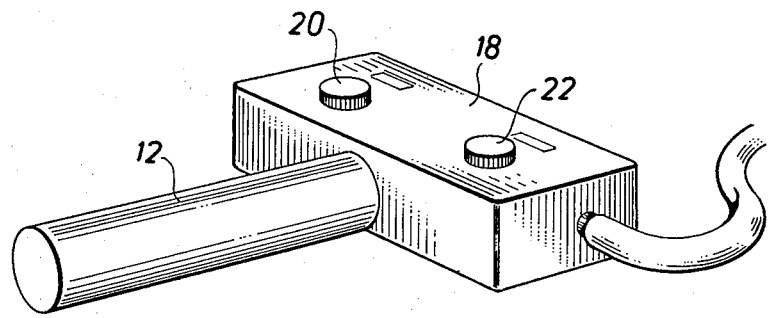
Figure 5:
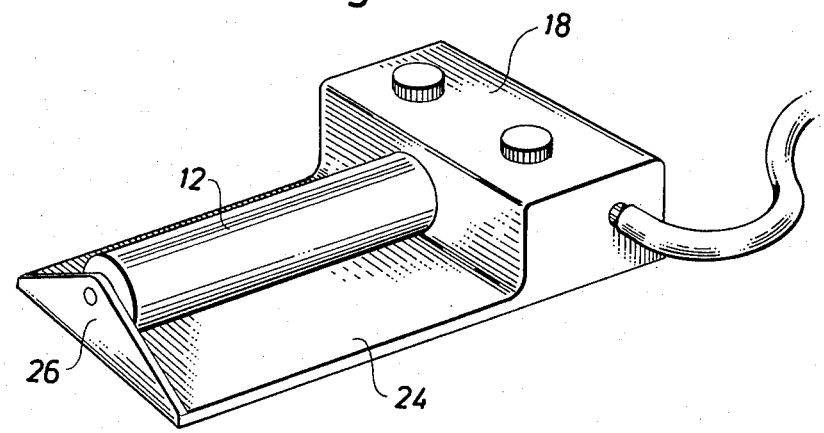

The invention will now be described more closely below with reference to the attached drawings, on which FIGS. 1-3 in a plan view, a side view and end view, respectively, illustrate a first embodiment of a regulating device according to the invention for pressure fluid actuated apparatus, and FIGS. 4 and 5 illustrate two further embodiments.

Figure 2:
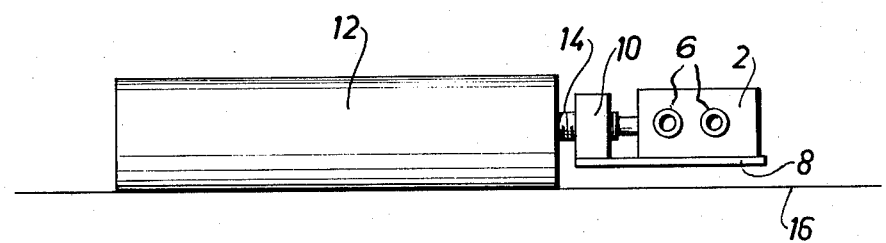

In FIGS. 1-3 the valve housing of a valve intended for regulating the air supply to e.g. an air operated dental drilling machine is indicated at 2. The valve can be of a conventional type, and in the present embodiment it has been assumed that it is of the type, where the movable valve element is actuated by or is a spring loaded, linearly movable piston. This piston is shown protruding out of the valve house 2 at 4. At 6 inputs and outputs for the pressurized fluid, e.g. air, are shown. The valve house 2 is mounted on a plate 8. The plate 8 carries a bearing box 10 (shown in section) with a screw threaded hole located in line with the piston 4.

A roller 12 intended for foot operation carries at one of its ends a coaxial screw 14 which is threaded into the threaded hole of the bearing box 10 into end contact with the piston 4.

In use the roller 12 is placed in the way illustrated in FIGS. 2 and 3 on a floor 16 and carries quite simply the plate 8 with the elements mounted thereon. For operating the valve and thereby regulating the pressurized fluid flow affected thereby, the roller 12 is rolled on the floor 16 by the foot of the operator, the plate 8 then bearing against the floor at one or the other of its edges extending parallel to the roller. Thereby the rolling movement provides a screwing movement of the screw 14, the axial component of which urges the piston 4 in the one or the other direction depending upon the direction of the rolling movement.

It should be easily understood that it is possible to obtain by means of the rolling movement and the transmission thereof to the movable valve element, very small and exact motions, and thereby an accurate adjustment of the valve element. Besides this purely structural advantage based upon the "gear change" between the foot and the valve element, man's foot is very sensible to rolling movements.

In the embodiment according to FIG. 4 elements 2-10 have been built into an outer housing 18. At 20 and 22 regulating knobs for regulating the water cooling and cleaning off air in a pressurized air operated dental drilling machine of the modern type are indicated.

FIG. 5 illustrates a further modification, wherein the housing 18 is mounted on a plate 24, which at its ends remote from the housing 18 carries a bearing support 26 for the corresponding end of the roller 12. In this embodiment the roller is thus not intended to be rolled directly on the floor.

How the foot shall be applied onto the roller in order to obtain a movement as comfortable and easy as possible for the user depends upon his posture otherwise. Normally the roller is, however, rolled in the most comfortable and simple way by a sitting or standing person by supporting the heel on the floor in front of the free end of the roller and keeping the foot essentially parallel to the roller so that it will rest essentially against the edge of the end of the roller.

The invention is not restricted to the embodiment shown on the drawing and described above, but can be modified within the scope of the following claims.

The type of transmission for transmitting the rolling movement to the movable valve element thus depends on the valve structure. The rolling movement need not be provided by means of a roller of the kind illustrated but any rollable body is usable. As examples a sphere, an ellipsoid, a body in the form of a truncated cone, and so on, can be mentioned. Finally, it is not necessary that the valve housing and the roller are located near each other, but the rolling movement can be transmitted to a remotely located valve by means of a device of the Bowden-wire type.

What is to be claimed is:

1. A regulating device for pressurized fluid actuated apparatus comprising
    a valve for the pressurized fluid supply,
    said valve including a valve housing and a movable flow control valve element,
    a foot controlled operating device connected to move said movable valve element of the valve,
    said operating device comprising an axially elongated roller body and a base structure,
    said valve housing being rigidly connected to said base structure,
    the outer cylindrical surface of said roller body being suitable and intended for resting on the floor and for rolling thereon when pushed by the foot of the operator,
    said roller body having a shaft coaxial with the rolling axis of said roller body and rotatably journalled in said base structure and operable for carrying said base structure and said valve housing for translational movement with said roller as said roller is rolled,
    said base structure having a dimension transverse to said rolling axis that exceeds the greatest transverse dimension of the roller body so as to limit rotational movement of said base structure about a horizontal axis when said roller body is rolled on the floor to thereby provide for relative rotational movement between said roller body and said base structure, and said shaft comprising a transmission means connected between said roller body and said valve element and arranged for transferring relative rotational movement between said roller body and said base structure to a movement of said valve element.

2. A device according to claim 1 wherein said valve, said base structure and said roller body are combined in a single unit intended to be placed on the floor for foot operation.

3. A device according to claim 2 wherein said shaft comprises an axial screw extending from one end thereof, said base structure including a screw-threaded bearing box engaging with the threads of said axial screw of said roller body, said axial screw and said screw threaded bearing box comprising said transmission means, said axial screw being engageable with said movable valve element to provide movement of said movable valve element in response to the axial movement of said axial screw in relation to said base structure upon rolling movement of said roller body by the operator.

4. A device as claimed in claim 3 wherein said movable valve element comprises an axially movable valve piston and wherein said means interconnecting said roller body and said movable valve element comprises the axial end of said axial screw in abutting engagement with an axial end of said movable valve element.

5. A device as claimed in claim 1 wherein said pressurized fluid actuated apparatus is a pressurized air operated dental drilling machine and said valve is connected to continuously regulate, by the position of its movable flow control valve element, the drill speed of the dental drilling machine.

* * * * *